(12) United States Patent
Li et al.

(10) Patent No.: US 9,067,957 B2
(45) Date of Patent: Jun. 30, 2015

(54) METAL NICKEL-IMIDAZOLATE CHIRAL NANO CLATHRATE COMPLEX AND PREPARATION METHOD THEREOF

(75) Inventors: Dan Li, Shantou (CN); Xiaoping Zhou, Shantou (CN); Jie Liu, Shantou (CN)

(73) Assignee: Golight, Inc., Culbertson ( * ) Notice: Subject to any disclaimer, the term of this patent is extended or adjusted under 35 U.S.C. 154(b) by 0 days.

(21) Appl. No.: 14/343,235

(22) PCT Filed: Sep. 14, 2011

(86) PCT No.: PCT/CN2011/079647
§ 371 (c)(1),
(2), (4) Date: Mar. 6, 2014

(87) PCT Pub. No.: WO2013/033922
PCT Pub. Date: Mar. 14, 2013

(65) Prior Publication Data
US 2014/0220349 A1    Aug. 7, 2014

(30) Foreign Application Priority Data

Sep. 7, 2011  (CN) .......................... 2011 1 0263178

(51) Int. Cl.
*C07F 15/04*   (2006.01)
(52) U.S. Cl.
CPC ......... *C07F 15/045* (2013.01); *Y10T 428/2982* (2015.01)
(58) Field of Classification Search
CPC .................. Y10T 428/2982; C07F 15/045
See application file for complete search history.

(56) References Cited

U.S. PATENT DOCUMENTS

2008/0161568 A1   7/2008  Chi et al.

FOREIGN PATENT DOCUMENTS

CN         101591360 A      12/2009

OTHER PUBLICATIONS

Liu et al., "Engineering Homochiral Metal-Organic Frameworks for Heterogeneous Asymmetric Catalysis and Enantioselective Separation," *Advanced Materials*, 2010, vol. 22, pp. 4112-4135.
Narasimhan et al., "Chiral Molecules with Polyhedral T, O, or I Symmetry: Theoretical Solution to a Difficult Problem in Stereochemistry," *CHIRALITY*, 2008, vol. 20, pp. 878-884.
Fiedler et al., "Selective Molecular Recognition, C-H Bond Activation, and Catalysis in Nanoscale Reaction Vessels," *Accounts of Chemical Research*, vol. 38, No. 4, 2005, pp. 351-360.
Pluth et al, "Proton-Mediated Chemistry and Catalysis in a Self-Assembled Supramolecular Host," *Accounts of Chemical Research*, vol. 42, No. 10, Oct. 2009, pp. 1650-1659.
Seeber et al., "Supramolecular Chirality in Coordination Chemistry," *Top Curr. Chem.* (2006) 265: pp. 147-183.
Ma et al., "Enantioselective catalysis with homochiral metal-organic frameworks,"*Chem. Soc. Rev.*, 2009, vol. 38, pp. 1248-1256.
Wang et al., "Preparation of nano Ni catalyst in ionic liquids [bmim] $PF_6$ and its application in the styrene hydrogenation," *Journal of Functional Materials*, vol. 39, No. 3, 2008, pp. 519-522.

*Primary Examiner* — Joseph Kosack

(57) ABSTRACT

The present invention discloses a metal nickel-imidazolate chiral nano clathrate complex and preparation method thereof. The new type of metal nickel-imidazolate chiral nano clathrate complex of the present invention has the following chemical formula: $[Ni_{14}(Im)_{24}]\cdot 4NO_3$, in which Im is N-1-methyl-(4-imidazole) methylene imine. The complex can be obtained directly from a reaction of starting materials or prepared through first initiating a reaction between the compound ligand Im and a nickel salt under solvothermal conditions, and the complex obtained is of higher purity. The nano clathrate complex of the present invention has single chirality, and higher thermal stability, and thus has potential application in chiral catalytic materials.

3 Claims, 5 Drawing Sheets

METAL NICKEL-IMIDAZOLATE CHIRAL NANO CLATHRATE COMPLEX AND PREPARATION METHOD THEREOF

BACKGROUND OF THE INVENTION (a) Field of the Invention

The present invention relates to the field of transition metal complex materials, involving porous metal complex materials, and in particularly to a metal-imidazolate chiral nano clathrate complex and preparation method thereof.

(b) Description of the Prior Art

Because the synthesis and preparation of chiral complexes have extensive application prospects in the fields of chiral catalysis, separation, and synthetic drugs, it has thus given rise to widespread interest among scientists, and has become a leading field of research for chemists around the world (such as: a) Y. Liu, W. Xuan, Y. Cui, *Adv. Mater.* 2010. 22. 4112-4135; b) L. Ma, C. Abney, W. Lin, *Chem. Soc. Rev.* 2009. 38. 1248; c) G. Seeber, B. E. F. Tiedemann, K. N. Raymond, *Top. Curr. Chem.* 2006. 265. 147-183). Traditional research on chiral complexes all use chiral organic ligands with metal-salt ligands to synthesize mononuclear or polynuclear complexes. However, because homochiral ligands are extremely expensive, thus, the manufacturing cost of chiral complexes is correspondingly high. In recent years, non-chiral ligand complexes have been used to construct chiral complexes through stereochemistry. In particular, chiral clathrate complexes have aroused great interest not only because of the distinctive supramolecular chemistry of their own chiral complex molecules, but also, more importantly, because of their huge application potential in the fields of chiral catalysis and separation (for example: a) D. Fiedler, D. H. Leung, R. G. Bergman, K. N. Raymond, *Acc. Chem. Res.* 2005. 38. 349-358; b) M. D. Pluth, R. G. Bergman, K. N. Raymond, *Acc. Chem. Res.* 2009. 42.1650-1659). Although chiral supramolecular clathrate complexes based on non-chiral ligands have been reported, however, the high nuclear, high symmetrical chiral clathrate filled complexes are still relatively rare (e.g. having O, I molecular point groups), and their synthesis remains a major challenge to chemists (S K Narasimhan, X. Lu. Y.-Y. Luk, *Chirality.* 2008. 20. 878-884). Because of their use in the development of chiral catalysis, simulation of biological enzymes, and chiral separation materials, the synthesis and exploration of such chemical compounds, especially chiral clathrate complexes that have high symmetry through rational design, will have a great impact on the development of high-performance materials, and will inject enormous life into the entire science of complex materials and catalysis.

SUMMARY OF THE INVENTION

The object of the present invention is to provide a metal nickel-imidazolate chiral nano clathrate complex with high symmetry.

Another object of the present invention lies in the preparation method of the metal nickel-imidazolate chiral nano clathrate complex.

The technical proposal of the present invention is as follows: A metal nickel-imidazolate chiral nano clathrate complex with the following general formula: $[Ni_{14}(Im)_{24}] \cdot 4NO_3$, and the structural schematic view of the complex structure is as shown in the figure below:

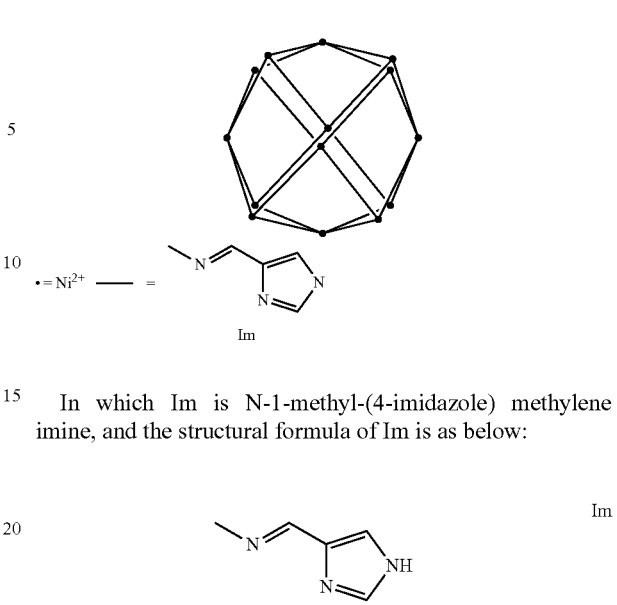

In which Im is N-1-methyl-(4-imidazole) methylene imine, and the structural formula of Im is as below:

The major infrared absorption peaks of the complexes described in the present invention were as follows:
2952.1w, 1685.8w, 1625.3s, 1542.4m, 1477.5m, 1384.2vs, 1335.9w, 1254.7m, 1206.8w, 1110.5s, 1035.8m, 1017.7m, 851.0w, 821.9m, 802.2w, 654.8m, 517.4w, 454.7w.

Crystals of the metal nickel-imidazolate chiral nano clathrate complex of the present invention belong to a cubic crystal system, with space group: P432, cell parameters: $a=b=c=16.2323(5)$ Å, $\alpha=\beta=\gamma=90°$, and $V=4277.0(2)$ Å3. In which two crystals of asymmetric nickel atoms respectively adopt a six-coordinate octahedral configuration and a four-coordinate square-planar configuration. A nickel-imidazolate nano clathrate chiral complex having O symmetry was formed through chelation of 24 Im ligands and 14 metal nickel ions, and bridging ligands. The size of the nickel-imidazolate nano clathrate chiral complex was 1.5 nm (nanometer). And the polyhedral structure of a Λ chiral configuration constructed by chelated nickel ions and Im ligands was shown to be a 24-face configuration.

Method 1 of synthesizing the metal nickel-imidazolate chiral nano clathrate complex of the present invention.

The preparation method comprises the following steps: Dissolving a mixture of an organic ligand 4-imidazole formaldehyde and the metal-salt $Ni(NO_3)_2 \cdot 6H_2O$ in a methanol solvent, and then adding drop by drop a methanol solution excessively dissolved with methylamine. Heating and allowing the resulting solution to react for 1 day, then collecting the precipitate, washing with methanol, and drying.

The molar ratio of the described 4-imidazole formaldehyde and metal-salt was from 1.5:1.0 to 2.0:1.0, with a preferred molar ratio of 1.5:1.0.

The heating temperature was from 60 to 80° C., with a preferred temperature of 70° C.

Method 2 of synthesizing the metal nickel-imidazolate chiral nano clathrate complex of the present invention.

The preparation method comprises the following steps: Dissolving a mixture of the organic ligand Im and the metal-salt $Ni(NO_3)_2 \cdot 6H_2O$ in a mixed solvent of N,N-dimethyl formamide/ethanol. Carrying out the reaction under solvothermal conditions, and then filtering the solution, collecting the crystals, washing with N,N-dimethyl formamide, and then drying the crystals.

The molar ratio of the described Im and metal-salt was from 1.5:1.0 to 2.0:1.0, with a preferred molar ratio of 1.5:1.0.

The volume ratio of N,N-dimethyl formamide and ethanol was from 4.0:1.0 to 3.0:1.0, with a preferred molar ratio of 4.0:1.0.

The heating temperature is from 100 to 120° C.

To enable a further understanding of said objectives and the technological methods of the invention herein, a brief description of the drawings is provided below followed by a detailed description of the preferred embodiments.

DETAILED DESCRIPTION OF THE PREFERRED EMBODIMENTS

Concrete embodiments for the synthesis of the metal nickel-imidazolate chiral nano clathrate complex Embodiment 1

0.5 mmol (millimole) of 4-imidazole formaldehyde and 0.32 mmol of nickel nitrate were dissolved in 5.0 ml (milliliter) of methanol, then heated and stirred in a 60° C. water bath for one hour, whereafter a 25% methylamine/methanol solution (1.6 mmol) was added. After heating in a 60° C. water bath for one day, the precipitate was collected, filtered, and then washed with methanol to obtain the target product. The yield was 60%.

Embodiment 2

A mixture of 0.04 mmol of $Ni(NO_3)_2\cdot 6H_2O$, 0.06 mmol of ligand Im and 2.0 ml of N,N-dimethyl formamide/ethanol (volume ratio of 4.0:1.0) was sealed in a hard glass tube (inside diameter 8.0 mm, outside diameter. 9.0 mm), which was placed in an oven at 120° C. and heated for 72 hours. After which, the temperature was allowed to fall to room temperature at a rate of 5° C./h (hour). The crystals were then collected, washed using N,N-dimethyl formamide, and then dried to obtain the target product. The yield was 45%.

Embodiment 3

A mixed solvent of 3.0 mmol of $Ni(NO)_2\cdot 6H_2O$ and 4.5 mmol of ligand Im was dissolved in 160 ml of N,N-dimethyl formamide/ethanol (volume ratio of 4.0:1.0), and the mixture was stirred to dissolve the components. The resulting solution was divided into ten portions, which were separately poured into 10 small 20.0 ml (milliliter) bottles. The bottles were placed in an oven at 120° C. and heated for 72 hours, after which the temperature was allowed to fall to room temperature at a rate of 5° C./h. The crystals were then collected, washed using N,N-dimethyl formamide, and then dried to obtain the target product. The yield was 53%.

Embodiment 4

Figure 3:
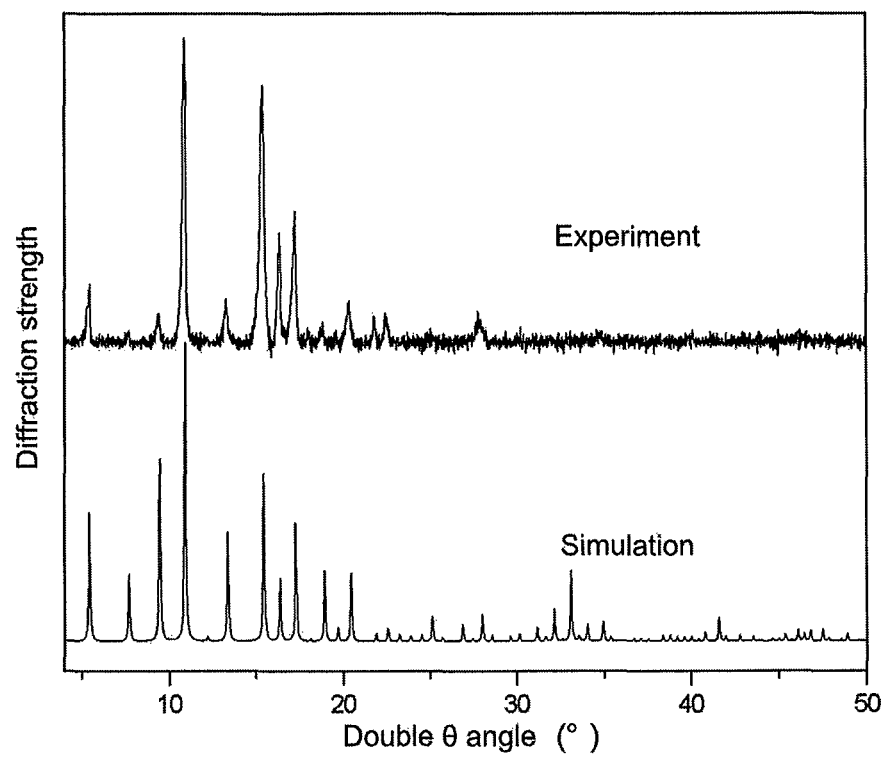
FIG. 3 shows powder diffraction spectra of the complex $[Ni_{14}(Im)_{24}]\cdot 4NO_3$ of the present invention.

(1) Characteristics and purity of X-ray powder diffraction: FIG. 3 shows an X-ray powder diffraction pattern for the complex $[Ni_{14}(Im)_{24}]\cdot 4NO_3$ of the present invention. Powder diffraction data was collected on a Bruker D8 advance diffractometer. The operating voltage of the instrument was 40 KV (kilovolt), current was 40 mA (milliampere), and used graphite monochromatic copper radiation (Cu Kα, λ=1.5418 Å (angstrom)). Continuous scanning was completed within a range of 5° to 50°, and Mercury software was used to simulate conversion of powder diffraction spectra from the crystal structure.

Figure 4:
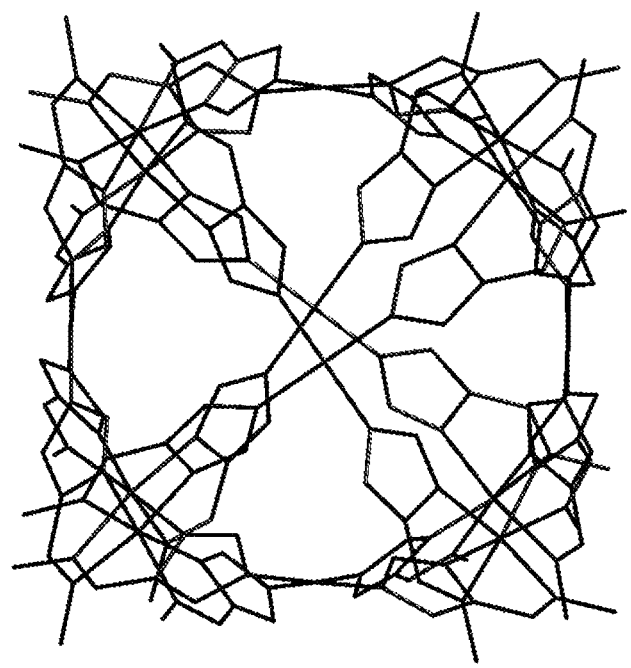
FIG. 4 shows a single crystal structural view of the complex $[Ni_{14}(Im)_{24}]\cdot 4NO_3$ of the present invention.
Figure 5:
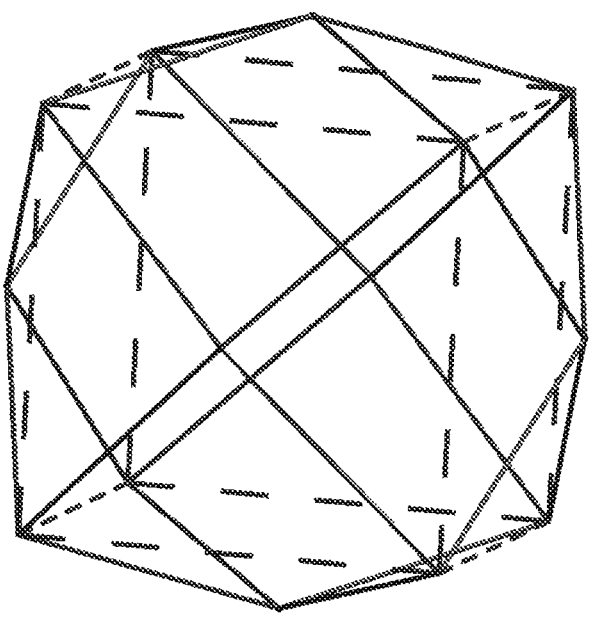
FIG. 5 shows a simplified 24-face structural view of the complex $[Ni_{14}(Im)_{24}]\cdot 4NO_3$ of the present invention.

(2) Determination of Crystal structure: The appropriate crystal size was selected under a microscope. The X-rays were monochromatized by passing through a graphite monochromator on an Agilent's Gmini A diffractometer (Cu Kα, λ=1.5418 Å), and the data was processed using the diffractometer program CrysAlis$^{Pro.1}$. A direct method was used to determine the initial structure model. Then the structure was refined using a method of least squares based on F2. Each isometric refinement was carried out on all non-hydrogen atoms, and theoretical hydrogenation was used to confirm the position of the hydrogen atoms. The nitrate ions were in a highly disordered state, and thus processed using the SQEEZE program of the PLATON software. FIG. 4 shows a crystal structural view of the complex $[Ni_{14}(Im)_{24}]\cdot 4NO_3$ of the present invention with the nitrate ions omitted. A portion of parameters of collected crystallographic diffraction data and structure refinements are listed in Table 1.

Figure 1:
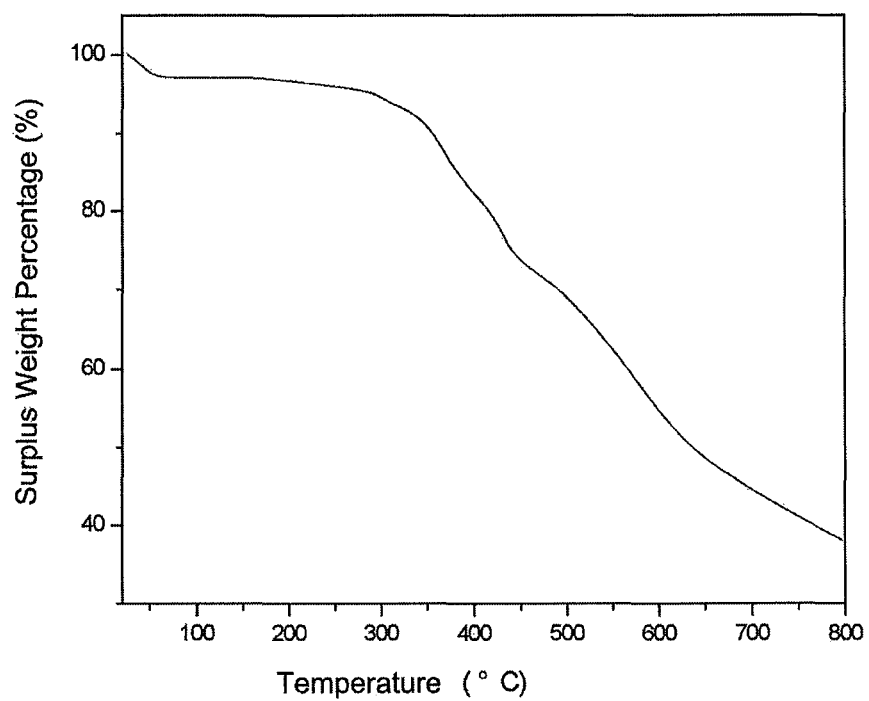
FIG. 1 shows a thermal analysis graph of the complex $[Ni_{14}(Im)_{24}]\cdot 4NO_3$ of the present invention.
Figure 2:
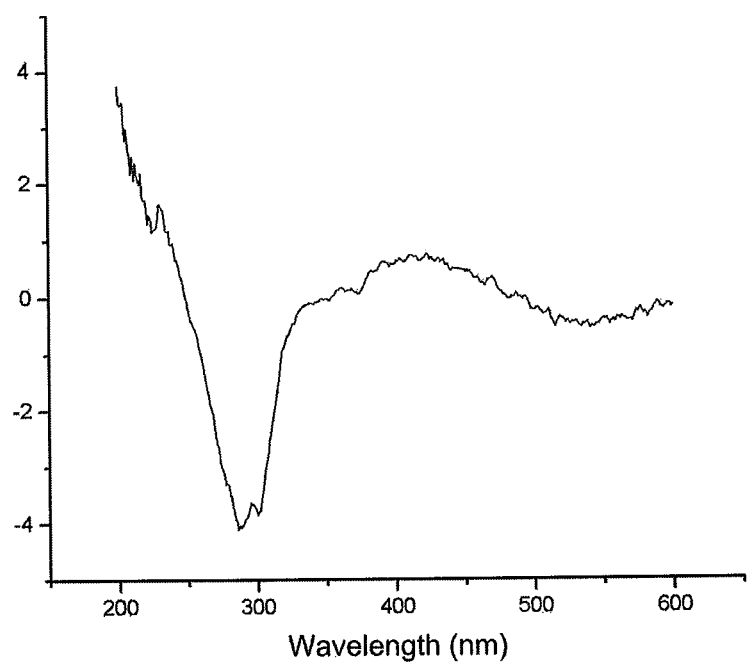
FIG. 2 shows a solid-state CD (Circular Dichroism) spectral graph of the complex $[Ni_{14}(Im)_{24}]\cdot 4NO_3$ of the present invention.

Thermal analysis experiments on the present invention showed that the metal nickel-imidazolate chiral nano clathrate complex had an extremely high thermal stability, and only began to decompose when the temperature reached 380 degrees Celsius (see FIG. 1). Solid-state CD (Circular Dichroism) spectra (FIG. 2) experiments showed that the complex was optically active. Therefore, the complex is a compound with supramolecular chirality, and can be used as a potential chiral catalysis and chiral separation material.

The complex of the present invention is a nano-sized chiral clathrate compound, and has potential applications in chiral catalysts, such as epoxidation of olefins catalyzed by chiral complexes and catalytic reduction of carbon monoxide to produce formaldehyde. Because of the clathrate structural characteristics of the chiral complexes, and the metal nickel atoms having vacant active sites, thus, the complex of the present invention provides the potential for higher catalytic efficiency and better dimensional selectivity.

TABLE 1

| Crystallographic data for metal nickel-imidazolate chiral nano clathrate complex | |
|---|---|
| | $[Ni_{14}(Im)_{24}]\cdot 4NO_3$ |
| Empirical formula | $C_{120}H_{144}N_{76}Ni_{14}O_{12}$ |
| Molecular weight | 3664.6 |
| Crystal system | cubic |
| Temperature (K) | 293.3 |
| Space group | P432 |
| Cell parameters | |
| a (Å) | 16.2323(5) |
| b (Å) | 16.2323(5) |
| c (Å) | 16.2323(5) |

TABLE 1-continued

Crystallographic data for metal nickel-imidazolate chiral nano clathrate complex

| | $[Ni_{14}(Im)_{24}]\cdot 4NO_3$ |
|---|---|
| α (deg) | 90 |
| β (deg) | 90 |
| γ (deg) | 90 |
| V (Å$^3$) | 4277.0(2) |
| Z | 1 |
| Theoretical density (g cm$^{-3}$) | 1.327 |
| Absorption coefficient (mm$^{-1}$) | 2.104 |
| Total diffraction points | 3159 |
| Independent diffraction points | 1184 |
| $R_{int}$ | 0.0642 |
| $R_1$ [I > 2σ(I)]$^a$ | 0.1067 |
| $wR_2$ [I > 2σ(I)]$^b$ | 0.2530 |
| $R_1$ [all data] | 0.1610 |
| $wR_2$ [all data] | 0.2877 |

$^a R_1 = \Sigma(||F_0| - |F_c||)/\Sigma|F_0|$;
$^b wR_2 = [\Sigma w(F_0^2 - F_c^2)^2/\Sigma w(F_0^2)^2]^{1/2}$ It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. A metal nickel-imidazolate chiral nano clathrate complex, comprising the formula: $[Ni_{14}(Im)_{24}]\cdot 4NO_3$, wherein Im is N-1-methyl-(4-imidazole) methylene imine;

wherein crystals of the metal nickel-imidazolate chiral nano clathrate complex belong to a cubic crystal system, space group is P432, cell parameters are a=b=c=16.2323 (5) Å (angstrom), α=β=γ=90°, and V=4277.0(2) Å$^3$;

wherein two crystals of asymmetric nickel atoms respectively adopts a six-coordinate octahedral configuration and a four-coordinate square-planar configuration; a nickel-imidazolate chiral nano clathrate complex having O symmetry is formed through chelation of 24 Im ligands and 14 metal nickel ions, and bridging ligands, the size of the nickel-imidazolate chiral nano clathrate complex is 1.5 nm (nanometer);

a Λ chiral configuration is constructed by chelated nickel ions and Im ligands; and the polyhedral structure of the metal nickel-imidazolate chiral nano clathrate complex is shown to be a 24-face configuration.

2. A preparation method of a metal nickel-imidazolate chiral nano clathrate complex, wherein the operation procedure comprises the following steps:

a) dissolving a mixture of the organic molecule 4-imidazole formaldehyde and the metal-salt $Ni(NO_3)_2\cdot 6H_2O$ in a methanol solvent, wherein the molar ratio of the 4-imidazole formaldehyde and the metal-salt $Ni(NO_3)_2\cdot 6H_2O$ is from 1.5:1.0 to 2.0:1.0, and the heating reaction temperature is from 60 to 80° C.;

b) adding drop by drop methanol solution dissolved with methylamine, heating and allowing to react for 1 day, then collecting the precipitate, washing with methanol, and drying.

3. A preparation method of a metal nickel-imidazolate chiral nano clathrate complex of claim 1, wherein the operation procedure comprises the following steps: mixing together the organic ligand Im and the metal-salt $Ni(NO_3)_2\cdot 6H_2O$ in the molar ratio of 1.5:1 to 2.0:1.0, and then dissolving the mixture in a mixed solvent of N,N-dimethyl formamide/ethanol, allowing a reaction to occur under solvothermal conditions, then filtering the solution, collecting the crystals, washing the crystals with N,N-dimethyl formamide, and drying; wherein the volume ratio of the N,N-dimethyl formamide and ethanol is from 4.0:1.0 to 3.0:1.0, and the heating reaction temperature is from 100 to 120° C.

* * * * *